United States Patent
Kondo

(10) Patent No.: US 11,547,653 B2
(45) Date of Patent: Jan. 10, 2023

(54) LIP COSMETIC

(71) Applicant: SHISEIDO COMPANY, LTD., Tokyo (JP)

(72) Inventor: Mika Kondo, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 132 days.

(21) Appl. No.: 16/638,940

(22) PCT Filed: Aug. 29, 2018

(86) PCT No.: PCT/JP2018/031923
§ 371 (c)(1),
(2) Date: Feb. 13, 2020

(87) PCT Pub. No.: WO2019/044895
PCT Pub. Date: Mar. 7, 2019

(65) Prior Publication Data
US 2020/0222301 A1    Jul. 16, 2020

(30) Foreign Application Priority Data
Aug. 31, 2017    (JP) .............................. JP2017-166382

(51) Int. Cl.
*A61Q 1/04*    (2006.01)
*A61Q 1/06*    (2006.01)
*A61K 8/891*    (2006.01)
*A61K 8/25*    (2006.01)
*A61K 8/26*    (2006.01)
*A61K 8/73*    (2006.01)
*A61K 8/86*    (2006.01)
*A61K 8/87*    (2006.01)
*A61K 8/88*    (2006.01)
*A61K 8/92*    (2006.01)
*A61K 8/96*    (2006.01)

(52) U.S. Cl.
CPC ................ *A61K 8/891* (2013.01); *A61K 8/25* (2013.01); *A61K 8/26* (2013.01); *A61K 8/731* (2013.01); *A61K 8/86* (2013.01); *A61K 8/87* (2013.01); *A61K 8/88* (2013.01); *A61K 8/92* (2013.01); *A61K 8/965* (2013.01); *A61Q 1/06* (2013.01)

(58) Field of Classification Search
None
See application file for complete search history.

(56) References Cited

U.S. PATENT DOCUMENTS

2015/0313812 A1    11/2015    Rubinson
2019/0350835 A1    11/2019    Konishi

FOREIGN PATENT DOCUMENTS

| CN | 110234312 A | 9/2019 |
|---|---|---|
| EP | 3578165 A1 | 12/2019 |
| JP | 60248604 A | 12/1985 |
| JP | 11269039 A2 | 10/1999 |
| JP | 2000281532 A2 | 10/2000 |
| JP | 2003286135 A | 10/2003 |
| JP | 201024163 A | 2/2010 |
| JP | WO2018143061 A1 | 11/2019 |
| KR | 20190110130 A | 9/2019 |
| WO | 2017/135629 A1 | 8/2017 |
| WO | 2018143061 A1 | 8/2018 |

OTHER PUBLICATIONS

International Search Report (ISR) issued in PTC/JP2018/031923 dated Dec. 4, 2018.
"Tractor Repair, Part IV, Old Parts Repair Process", Tractor Repair Writing Group, Machinery Industry Press, 1979, p. 167, 1st edition, Cited in CNOA; English machine translation of CNOA as a concise explanation of the relevance.

*Primary Examiner* — Jyothsna A Venkat
(74) *Attorney, Agent, or Firm* — Rankin, Hill & Clark LLP

(57) ABSTRACT

An object of the present invention is to provide a lip stick which can produce the excellent usability and plumps up lips while appropriately suppressing the gloss of lips in makeup finish upon application. The lip cosmetic is characterized by including: (A) 12 to 35 mass % of a powder composition except for a color pigment, the powder composition including one or two or more selected from a silicone powder, a urethane powder, and a nylon powder in an amount of 40 mass % or more; and (B) 50 to 68 mass % of a fluid oil content having a viscosity of 15 to 100 mPa·s, the fluid oil content including an oil content having a viscosity of 15 to 100 mPa·s in an amount of 44 mass % or more.

2 Claims, No Drawings

＃ LIP COSMETIC

TECHNICAL FIELD

The present invention relates to a lip cosmetic capable of achieving excellent usability and plumping up lips while appropriately suppressing the gloss of lips in makeup finish upon application of the lip cosmetic.

BACKGROUND ART

The cosmetic effect by a lipstick is very high as compared to other makeup items. Accordingly, various lipsticks have been conventionally developed. This results in a so-called matte lipstick suppressing the gloss, and providing finish having matte feeling, other than general lipsticks imparting gloss to lips.

Such a matte lipstick includes a large amount of a powder having a high covering power or a white pigment added therein, and suppresses the reflection of a light. However, addition of such a powder increases the hardness of the lipstick, so that the lipstick becomes more likely to slip on the surface of lips, and hence tends to become less likely to be applied. Further, such superficial feel tends to impair the sense of luxury required of the cosmetic.

Further, the matte lipstick allows less light to transmit therethrough, which tends to result in unnatural finish. Accordingly, it is difficult to sufficiently plump up lips.

This created a demand for the development of a lip cosmetic capable of achieving excellent usability and plumping up lips while appropriately suppressing the gloss of lips in makeup finish upon application.

[PTL 1] Japanese Patent Application Publication No. H11-269039

SUMMARY OF INVENTION

Technical Problem

It is an object of the present invention to provide a lip cosmetic capable of producing the excellent usability and plumping up lips while appropriately suppressing the gloss of lips in makeup finish upon application.

Solution to Problem

In order to solve the problem, the present inventors conducted a study. As a result, the present inventors found the following: by adding prescribed powder composition and fluid oil content each in a prescribed amount, it is possible to achieve excellent usability and to plump up lips while appropriately suppressing the gloss of lips, leading to the completion of the present invention.

Namely, the present invention relates to a lip cosmetic, including: (A) 12 to 35 mass % of a powder composition except for a color pigment, the powder composition including one or two or more selected from a silicone powder, a urethane powder, and a nylon powder in an amount of 40 mass % or more; and (B) 50 to 68 mass % of a fluid oil content having a viscosity of 15 to 100 mPa·s, the fluid oil content including an oil content having a viscosity of 15 to 100 mPa·s in an amount of 44 mass % or more.

Further, the present invention relates to the lip cosmetic wherein the glossiness of a coating film thereof having an area of 1 mg/cm$^2$ is 71 or less.

Advantageous Effects of Invention

In accordance with a lip cosmetic of the present invention, it is possible to achieve excellent usability and plump lips while achieving finish having appropriately suppressed gloss, and matte feeling upon application.

DESCRIPTION OF EMBODIMENTS

The lip cosmetic of the present invention includes: (A) 12 to 35 mass % of a powder composition except for a color pigment, the powder composition including one or two or more selected from a silicone powder, a urethane powder, and a nylon powder in an amount of 40 mass % or more; and (B) 50 to 68 mass % of a fluid oil content having a viscosity of 15 to 100 mPa·s, the fluid oil content including an oil content having a viscosity of 15 to 100 mPa·s in an amount of 44 mass % or more.

The lip cosmetic of the present invention contains, as a component (A), a powder composition except for a color pigment in an amount of 12 to 35 mass %. The presence of prescribed amount of the component (A) can provide the excellent usability while appropriately suppressing the gloss of lips. When the amount of the component (A) is smaller than 12 mass %, spreading becomes too light. Conversely, when the component (A) is added in an amount of more than 35 mass %, spreading becomes too heavy, resulting in inferior usability.

The component (A) of the present invention includes one or two or more selected from a silicone powder, a urethane powder, and a nylon powder in an amount of 40 mass % or more. Addition of a silicone powder or the like in an amount of 40 mass % or more results in soft feel to lips, which can provide the excellent usability.

As the silicone powders for use in the present invention, mention may be made of (diphenyl dimethicone/vinyl diphenyl dimethicone/silsesquioxane) crosspolymer, (dimethicone/vinyl dimethicone) crosspolymer, (vinyl dimethicone/methicone silsesquioxane) crosspolymer, (diphenyl dimethicone/vinyl diphenyl dimethicone/silsesquioxane) crosspolymer, and the like. Examples of the commercially available products thereof may include KSP series (KSP-100, KSP-101, KSP-102, KSP-105, KSP-300, KSP-411, and KSP-441 (manufactured by Shin-Etsu Chemical Co., Ltd.), and the like. Further, as urethane powders, mention may be made of (HDI/trimethylolhexyl lactone) crosspolymer, (IPDI/poly(1,4-butane diol)-14) crosspolymer, and the like. As the commercially available products thereof, mention may be made of plastic powder D-400 (manufactured by Toshiki Pigment Co., Ltd.), UREPEARL US-01 (manufactured by Konishi Co., Ltd.). For a nylon powder, a spheroidal nylon powder commercially available as a nylon powder or the like is preferably used.

In accordance with the present invention, as the component (B), a fluid oil content with a viscosity of 15 to 100 mPa·s is added in an amount of 50 to 68 mass %. The viscosity is the measurement value at 30° C. Incidentally, for the measurement of the viscosity, a viscoelasticity measuring device manufactured by Anton Paar GmbH, can be used.

The fluid oil content of the component (B) includes an oil content with a viscosity of 15 to 100 mPa·s in an amount of 44 mass % or more. Examples of the oil content with a viscosity of 15 to 100 mPa·s may include olefin oligomer or hydrogenated polydecene (as a commercially available product thereof, for example, "NOMCORT HP-30" (manufactured by The Nisshin OilliO Group, Ltd.)), mineral oil (as a commercially available product thereof, for example, "High White 22S" (manufactured by Nippon Oil Corporation)), ethylhexyl palmitate (as a commercially available product thereof, for example, "SALACOS P-8" (manufactured by Patech Fine Chemicals Co., Ltd.)), cetyl ethylhexanoate (as a commercially available product thereof, for example, "NIKKOL CIO-JP" (manufactured by Nippon Surfactant Industries Co., Ltd.), trimethylolpropane triethyl hexanoate (as a commercially available product thereof, for example, "TA-TM-308" (manufactured by Nippon Fine Chemical Co., Ltd.)), triisostearin (as a commercially available product thereof, for example, "Sun Espol G-318" (manufactured by Taiyo Kagaku Co., Ltd.)), pentaerythrityl tetraethyl hexanoate (as a commercially available product thereof, for example, "RA-PE-408" (manufactured by Nippon Fine Chemical Co., Ltd.)), dimethicone (as a commercially available product thereof, for example, "KF-96A-2CS" (manufactured by Shin-Etsu Chemical Co., Ltd.), "KF-96L-1.5CS" (manufactured by Shin-Etsu Chemical Co., Ltd.), "Wacker-Belsil® DM 1 PLUS" (manufactured by Wacker Asahikasei Silicone Co., Ltd.), "KF-96A-6CS" (manufactured by Shin-Etsu Chemical Co., Ltd.)), cyclopentasiloxane (as a commercially available product thereof, for example, "EXECOL-D-5" (manufactured by Shin-Etsu Chemical Co., Ltd.), diphenylsiloxy phenyl trimethicone (as a commercially available product thereof, for example, "KF-56A" (manufactured by Shin-Etsu Chemical Co., Ltd.), octyl dodecanol (as a commercially available product thereof, for example, "NJCOL 200A" (manufactured by New Japan Chemical Co., Ltd.)), decyl tetradecanol (as a commercially available product thereof, for example, "NJCOL 240A" (manufactured by New Japan Chemical Co., Ltd.)), and neopentyl glycol dicaprate (as a commercially available product thereof, for example, "ESTEMOL N-01" (manufactured by The Nisshin OilliO Group, Ltd.)).

EXAMPLES

Below, a description will be given in details by way of Examples. However, the Examples are not intended to restrict the present invention. Incidentally, the numerical values in Tables are expressed in terms of mass % unless otherwise specified.

Each specimen can be prepared by an ordinary method to be used for a lip cosmetic. Each specimen was evaluated for the feeling in use and the outward appearance created upon applying a specimen to lips by ten expert panelists. From the results, evaluation was conducted according to the following criteria.

<Evaluation Criteria>
AA: evaluated as good by 8 or more panelists (success)
BB: evaluated as good by 7 or more panelists (success)
CC: evaluated as good by 4 to 6 panelists (success)
DD: evaluated as good by 3 or less panelists (failure)

TABLE 1

| | | | Comp. Ex. 1 | Ex. 1 | Ex. 2 | Ex. 3 | Ex. 4 | Comp Ex. 2 |
|---|---|---|---|---|---|---|---|---|
| (B) | Solid oil content | Polyethylene | 8.5 | 8.5 | 8.5 | 8.5 | 8.5 | 8.5 |
| | | Microcrystalline wax | 1.5 | 1.5 | 1.5 | 1.5 | 1.5 | 1.5 |
| | Fluid oil content | Diphenylsiloxy phenyl trimethicone *1 | — | 20 | 20 | 20 | 20 | 20 |
| | | Neopentyl glycol dicaprate *1 | 20 | 10 | 10 | 10 | 10 | 10 |
| | | Pentaerythrityl tetraethyl hexanoate *1 | 50 | 38 | 30 | 20 | 20 | 15 |
| (A)*2 | Powder | (Vinyl dimethicone/methicone silsesquioxane) crosspolymer *3 | 10 | 12 | 20 | 30 | 35 | 40 |
| | Organic pigment | Coloring material | 10 | 10 | 10 | 10 | 5 | 5 |
| | | Total | 100 | 100 | 100 | 100 | 100 | 100 |
| | | Amount of powder composition (A) | 10 | 12 | 20 | 30 | 35 | 40 |
| | | Amount of fluid oil content (B) | 70 | 68 | 60 | 50 | 50 | 45 |
| | | Viscosity (mPa · s) of fluid oil content (B) at 30° C. | 44 | 31 | 26.9 | 22.7 | 22.7 | 20.4 |
| | | Ratio (%) of fluid oil content of 15 to 100 mPa · s contained in fluid oil content (B) | 100 | 100 | 100 | 100 | 100 | 100 |
| | | Smoothness of spreading | DD too light | BB | BB | BB | BB | DD too heavy |
| | | Softness during application | BB | BB | BB | BB | BB | BB |

*1 Fluid oil content with a viscosity of 15 to 100 mPa · s
*2 Powder composition except for color pigment
*3 Silicone powder Table 1 shows the effects of the addition amounts of the powder and the fluid oil content exerted on the "smoothness of spread" and the "softness during application". From the results of Examples 1 to 4, it has been confirmed that addition of 12 to 35 mass % of a powder composition except for a color pigment, and 50 to 68 mass % of a fluid oil content can provide a good result.

TABLE 2

| | | | Ex. 5 | Ex. 6 | Ex. 7 | Ex. 8 | Comp. Ex. 3 | Comp. Ex. 4 | Comp. Ex. 5 |
|---|---|---|---|---|---|---|---|---|---|
| (B) | Solid oil content | Polyethylene | 8.5 | 8.5 | 8.5 | 8.5 | 8.5 | 8.5 | 8.5 |
| | | Microcrystalline wax | 1.5 | 1.5 | 1.5 | 1.5 | 1.5 | 1.5 | 1.5 |
| | Fluid oil content | Diphenylsiloxy phenyl trimethicone *1 | 20 | 20 | 20 | 20 | 20 | 20 | 20 |
| | | Neopentyl glycol dicaprate *1 | 10 | 10 | 10 | 10 | 10 | 10 | 10 |
| | | Pentaerythrityl tetraethyl hexanoate *1 | 30 | 30 | 30 | 30 | 30 | 30 | 30 |

TABLE 2-continued

|  |  |  | Ex. 5 | Ex. 6 | Ex. 7 | Ex. 8 | Comp. Ex. 3 | Comp. Ex. 4 | Comp. Ex. 5 |
|---|---|---|---|---|---|---|---|---|---|
| (A)*2 | Powder | (Dimethicone/vinyl dimethicone) crosspolymer *3 | 8 |  |  |  |  |  |  |
|  |  | (Vinyl dimethicone/methicone silsesquioxane) crosspolymer *3 |  | 20 |  |  |  |  |  |
|  |  | (IPDI/poly(1,4-butane diol)-14) crosspolymer *4 |  |  | 18 |  |  |  |  |
|  |  | Nylon-12 *5 |  |  |  | 20 |  |  |  |
|  |  | Silica |  |  |  | 2 |  |  |  |
|  | Extender pigment | Mica |  |  |  |  | 20 |  |  |
|  |  | Synthetic phlogopite |  |  |  |  |  | 20 |  |
|  |  | kaolin |  |  |  |  |  |  | 20 |
|  |  | talc | 12 |  |  |  |  |  |  |
|  | Color pigment | Coloring material | 10 | 10 | 10 | 10 | 10 | 10 | 10 |
|  |  | Total | 100 | 100 | 100 | 100 | 100 | 100 | 100 |
|  |  | Amount of powder composition (A) | 20 | 20 | 20 | 20 | 20 | 20 | 20 |
|  |  | Ratio (%) of silicone powder, urethan powder, or nylon powder in powder composition (A) | 40 | 100 | 90 | 100 | 0 | 0 | 0 |
|  |  | Amount of fluid oil content (B) | 60 | 60 | 60 | 60 | 60 | 60 | 60 |
|  |  | Viscosity (mPa · s) of fluid oil content (B) at 30° C. | 27.2 | 27.2 | 27.2 | 27.2 | 27.2 | 27.2 | 27.2 |
|  |  | Ratio (%) of fluid oil content of 15 to 100 mPa · s contained in fluid oil content (B) | 100 | 100 | 100 | 100 | 100 | 100 | 100 |
|  |  | Softness during application | AA | AA | BB | BB | DD | DD | DD |
|  |  | Smoothness of spreading | BB | BB | BB | BB | DD | DD | DD |
|  |  | Plumpness | BB | BB | BB | BB | DD | DD | DD |

*1 Fluid oil content with a viscosity of 15 to 100 mPa · s
*2 Powder composition except for color pigment
*3 Silicone powder
*4 Urethane powder
*5 Nylon powder Table 2 shows the results of a study on the effects of the kind and the addition amount of the powder forming the powder composition exerted on the "softness during application", the "smoothness of spread" and the "plumpness" after makeup. From the results of Examples 5 to 8, it has been confirmed as follows: by setting the ratio of the silicone powder, the urethan powder, or the nylon powder included in the powder composition except for a color pigment at 40 mass % or more, it is possible to provide a good result.

TABLE 3

|  |  |  | Ex. 9 | Ex. 10 | Ex. 11 | Ex. 12 | Ex. 13 | Ex. 14 | Ex. 15 | Ex. 16 | Comp. Ex. 6 | Comp. Ex. 7 | Comp. Ex. 8 |
|---|---|---|---|---|---|---|---|---|---|---|---|---|---|
| (B) | Solid oil content | Polyethylene | 8.5 | 8.5 | 8.5 | 8.5 | 8.5 | 8.5 | 8.5 | 8.5 | 8.5 | 8.5 | 8.5 |
|  |  | Microcrystalline wax | 1.5 | 1.5 | 1.5 | 1.5 | 1.5 | 1.5 | 1.5 | 1.5 | 1.5 | 1.5 | 1.5 |
|  | Fluid oil content | Diphenylsiloxy phenyl trimethicone *1 | 20 | 20 | 20 | 20 | 20 | 20 | 20 | 20 | 20 | 20 | 26.25 |
|  |  | Pentaerythrityl tetraethyl hexanoate *1 | 33 | 33 | 33 | 33 |  |  |  |  |  | 13 |  |
|  |  | Neopentyl glycol dicaprate *1 | 10 |  | 5 |  |  |  |  |  |  |  |  |
|  |  | Mineral oil *1 |  |  |  |  | 43 | 33 | 33 | 8 |  | 15 | 10.5 |
|  |  | Diisostearyl malate |  | 10 |  |  |  |  | 10 | 35 | 43 |  |  |
|  |  | Hydrogenated polyisobutene |  |  | 5 | 10 |  | 10 |  |  |  | 15 | 26.25 |
| (A)*2 | Powder | (Vinyl dimethicone/methicone silsesquioxane) crosspolymer *3 | 20 | 20 | 20 | 20 | 20 | 20 | 20 | 20 | 20 | 20 | 20 |
|  |  | Cellulose | 2 | 2 | 2 | 2 | 2 | 2 | 2 | 2 | 2 | 2 | 2 |
|  | Color pigment | Coloring material | 5 | 5 | 5 | 5 | 5 | 5 | 5 | 5 | 5 | 5 | 5 |
|  |  | Total | 100 | 100 | 100 | 100 | 100 | 100 | 100 | 100 | 100 | 100 | 100 |
|  |  | Amount of fluid oil content (B) | 63 | 63 | 63 | 63 | 63 | 63 | 63 | 63 | 63 | 63 | 63 |
|  |  | Viscosity (mPa · s) of fluid oil content (B) at 30° C. | 37.2 | 49.3 | 62.7 | 93.1 | 15.3 | 54.3 | 25.1 | 63 | 133 | 155 | 230 |
|  |  | Ratio (%) of fluid oil content of 15 to 100 mPa · s contained in fluid oil content (B) | 100 | 84 | 92 | 84 | 100 | 84 | 84 | 44 | 32 | 76 | 58 |

TABLE 3-continued

|  | Ex. 9 | Ex. 10 | Ex. 11 | Ex. 12 | Ex. 13 | Ex. 14 | Ex. 15 | Ex. 16 | Comp. Ex. 6 | Comp. Ex. 7 | Comp. Ex. 8 |
|---|---|---|---|---|---|---|---|---|---|---|---|
| Smoothness of spreading | BB | BB | BB | CC | BB | BB | BB | BB | DD | DD | DD |

*1 Fluid oil content with a viscosity of 15 to 100 mPa · s
*2 Powder composition except for color pigment
*3 Silicone powder Table 3 shows the effects of the viscosity of the fluid oil content exerted on the "smoothness of spread" during application. The viscosity of the fluid oil content shows the numerical value measured using a viscoelasticity measuring device manufactured by Anton Paar GmbH, at 30° C.

The results of Examples 9 to 16 shown in Table 3 indicate that, by setting the content of the fluid oil content of 15 to 100 mPa·s contained in the fluid oil content at 44 mass % or more, and setting the viscosity of the total fluid oil content at 15 to 100 mPa·s, it is possible to provide a good result.

TABLE 4

|  |  |  | Ex. 17 | Ex. 18 | Ex. 19 |
|---|---|---|---|---|---|
| | Solid oil content | Polyethylene | 8.5 | 8.5 | 8.5 |
| | | Microcrystalline wax | 1.5 | 1.5 | 1.5 |
| (B) | Fluid oil content | Diphenylsiloxy phenyl trimethicone *1 | 20 | 20 | 20 |
| | | Neopentyl glycol dicaprate *1 | 10 | 10 | 10 |
| | | Pentaerythrityl tetraethyl hexanoate *1 | 28 | 33 | 36 |
| (A)*2 | Powder | Dimethicone/vinyl dimethicone) crosspolymer *3 | 20 | 15 | 12 |
| | | Cellulose | 2 | 2 | 2 |
| | Color pigment | Coloring material | 10 | 10 | 10 |
| | | Total | 100 | 100 | 100 |
| | | Matte feeling | BB | BB | CC |
| | | Glossiness | 46 | 60 | 71 |
| | | Amount of powder composition (A) added | 22 | 17 | 14 |
| | | Ratio (%) of silicone powder, urethan powder, or nylon powder in powder composition (A) | 91 | 88 | 86 |
| | | Amount of fluid oil content (B) added | 58 | 63 | 66 |
| | | Viscosity (mPa · s) of fluid oil content (B) at 30° C. | 27.6 | 28.6 | 30.6 |
| | | Ratio (%) of fluid oil content of 15 to 100 mPa · s contained in fluid oil content (B) | 100 | 100 | 100 |

*1 Fluid oil content with a viscosity of 15 to 100 mPa · s
*2 Powder composition except for color pigment
*3 Silicone powder Table 4 shows the results of the study on the relationship between the addition amounts of the powder composition and the fluid oil content, and the matte feeling and the glossiness for imparting the matte feeling to a lip cosmetic. The glossiness is the numerical value obtained in the following manner: a specimen is uniformly applied on the surface of a PET film so that the thickness of the coating film becomes 1 mg/cm$^2$; the specimen is allowed to stand still for 1 hour under the condition of 25° C.; then, the measurement was conducted using a Gloss Meter VG2000 manufactured by Nippon Denshoku Industries Co., Ltd.

From the results of Examples 17 to 19 shown in Table 4, by adding a powder composition except for a color pigment in an amount of 14 mass % or more, it was possible to suppress the glossiness at 71 or less. As a result, it was possible to obtain excellent matte feeling.

The invention claimed is:
1. A lip cosmetic, comprising:
(A) 12 to 35 mass % of a powder composition except for a color pigment, the powder composition comprising a silicone powder, wherein the silicone powder is (vinyl dimethicone/methicone silsesquioxane) crosspolymer in an amount of 40 mass % or more with respect to the powder composition, ;
and (B) 50 to 68 mass % of a fluid oil content having a viscosity of 15 to 100 mPa·s, the fluid oil content comprising mixture of diphenylsiloxy phenyl trimethicone, neopentyl glycol dicaprate and pentaerythrityl tetraethyl hexanoate in an amount of 44 mass % or more with respect to the fluid oil content.
2.
The lip cosmetic according to claim 1, wherein a glossiness of a coating film thereof having an area of 1 mg/cm$^2$ is 71 or less.

* * * * *